(12) United States Patent
Kroll et al.

(10) Patent No.: US 7,164,950 B2
(45) Date of Patent: Jan. 16, 2007

(54) IMPLANTABLE STIMULATION DEVICE WITH ISOLATING SYSTEM FOR MINIMIZING MAGNETIC INDUCTION

(75) Inventors: Mark W. Kroll, Simi Valley, CA (US); Scott Salys, Canyon Country, CA (US); Timothy J. Cox, Friendswood, TX (US); Kerwyn Schimke, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 537 days.

(21) Appl. No.: 10/285,241

(22) Filed: Oct. 30, 2002

(65) Prior Publication Data

US 2004/0088012 A1    May 6, 2004

(51) Int. Cl.
*A61N 1/372* (2006.01)
(52) U.S. Cl. ....................................................... 607/36
(58) Field of Classification Search .................. 607/9, 607/4–5, 2, 36; 128/901
See application file for complete search history.

(56) References Cited

U.S. PATENT DOCUMENTS

| | | | | |
|---|---|---|---|---|
| 5,040,239 A | * | 8/1991 | Kondo et al. ............. | 455/193.1 |
| 5,697,958 A | * | 12/1997 | Paul et al. ..................... | 607/31 |
| 6,188,926 B1 | * | 2/2001 | Vock .............................. | 607/9 |
| 6,209,764 B1 | | 4/2001 | Hartlaub et al. .............. | 223/94 |
| 6,795,736 B1 | * | 9/2004 | Connelly et al. ............. | 607/36 |
| 6,901,292 B1 | * | 5/2005 | Hrdlicka et al. .............. | 607/27 |
| 6,937,906 B1 | * | 8/2005 | Terry et al. ................... | 607/63 |
| 2003/0204217 A1 | * | 10/2003 | Greatbatch ................... | 607/36 |

OTHER PUBLICATIONS

Section 7 (pp. 121-124), entitled "Magneto Resistors", of Infineon Technologies Data Book (Jul. 1, 2002).

* cited by examiner

*Primary Examiner*—Robert E. Pezzuto
*Assistant Examiner*—Jessica L. Reidel

(57) ABSTRACT

An implantable cardiac stimulation device is equipped with an isolation system capable of attenuating or eliminating induction currents flowing through the stimulation device by eliminating induction loops. The isolation system comprises a magnetic insulator configured to shield selected components of the stimulation device from external magnetic fields or radio-frequency (RF) signals. The magnetic insulator comprises a plurality of sensors that are configured to detect the intensity of the external magnetic fields and/or RF signals, and a switch bank that electrically isolates certain components of the stimulation device to eliminate the induction loops. The isolation system further comprises an attenuation system comprised of at least one magnetoresistor disposed along potential induction loops to attenuate induction currents when subjected to undesirable external magnetic fields and/or RF signals.

19 Claims, 7 Drawing Sheets

IMPLANTABLE STIMULATION DEVICE WITH ISOLATING SYSTEM FOR MINIMIZING MAGNETIC INDUCTION

FIELD OF THE INVENTION

The present invention generally relates to implantable cardiac stimulation devices. More specifically, the present invention relates to implantable cardioverter defibrillators that are equipped with insulation, isolation, and/or attenuation systems capable of minimizing induction currents flowing through the implantable devices, or eliminating induction loops through which the induced electric current flows.

BACKGROUND OF THE INVENTION

Implantable medical devices have been developed to support various body functions internally without having to connect wires through the skin. Examples of these devices include implantable pacemakers, cardioverters or defibrillators for monitoring and for stimulating ailing hearts. Implantable bladder stimulators provide electrical stimuli to bladder muscles to restore bladder function. Similar types of electrical stimuli provided by bone growth stimulators help the patients with complicated bone fractures. Cerebellar implantable devices monitor brain activities and stimulate the brain to control seizures in epilepsy as well as pain.

A common configuration of such implantable medical devices includes pulse generators with electronic circuitry contained in a housing and conductive leads that connect the pulse generators to the target organ or tissue. When the target organ or tissue also has a conductive path to the pulse generator, a conductive loop is established. Under normal usage of the device, no electric current flows through these conductive loops. When the patients implanted with the devices are subjected to external electromagnetic interference, however, undesirable electric current and voltage could be induced by such interference and could create undesirable physiological effects, such as fibrillation and pain.

Documented examples of medical device malfunctions have been traced to medical procedures, such as radiofrequency catheter ablation, electrocautary, dental procedures, magnetic resonance imaging (MRI) techniques, as well as other medical procedures. Of these well-known sources of electromagnetic interference, the MRI system is perhaps the most common.

MRI is a technique that provides a non-invasive method for the examination of the internal anatomy of a human body. This provides an efficient means for diagnosing disorders such as neurological and cardiac abnormalities. However, it may be unsafe and even hazardous to place patients implanted with the medical device through the MRI system because this may generate high radiofrequency (RF) signals, in the range of, for example, 64 MHz.

Such a high RF field may induce eddy currents on the conductive housing of the device, causing heat energy to be dissipated to the surrounding tissues, damaging them. More disadvantageously, the high RF field and resulting high induced voltage may demodulate the voltage within internal components of the implanted device. As a result, each RF pulse generated by the MRI system can generate voltage through the leads to the electrically excitable tissues.

In pacemakers or implantable cardioverter defibrillators (ICDs), the resulting high frequency output could, in certain cases, cause life-threatening fibrillation of the heart. Low energy voltage induced by the varying RF field may also inhibit the output of the pacing pulse to the patient. Such induction loops may exist in both the bipolar and unipolar lead configurations of the pacemaker or ICDs.

Several methods have been proposed to eliminate the effects of interference by the MRI systems on the implantable medical devices. In one such method a switching system provides high impedance to the conductive loop when a magnetic field above a preset threshold is detected. In another method an internal electronic circuitry is encased in a metal housing that is hermetically sealed to shield off external electromagnetic fields. Other methods propose using looped wires to offset stray RF fields and active RF filter to filter out a preselected range of RF frequency.

However, the foregoing methods provide only static isolation of undesirable interference from the implantable devices, and in some cases, the methods used to render the implanted device compatible with the operation of the MRI limit the ability of the implanted device to monitor external activities and to provide therapy at the preset time. Thus, it would be desirable to provide a dynamic approach that maximizes the magnetic and tuned RF detection response, while maintaining the integrity of the normal function of the implanted medical device. The need for such a design has heretofore remained unsatisfied.

SUMMARY

The present invention addresses the foregoing need by providing an implantable stimulation device, such as an implantable cardioverter defibrillator (ICD), with a dynamic isolation system that includes insulation, isolation, and/or attenuation devices arranged to minimize induction currents flowing through the implantable devices and/or to eliminate induction loops through which the induced electric current flows.

A typical implantable device is comprised of a pulse generator that generates an electrical pulse, an electrode in electrical contact with the heart, and at least one lead connecting the pulse generator to the electrode to deliver electrical pulses from the pulse generator to the heart. Induction loops are generally formed by an external magnetic field and/or a radio frequency (RF) signal applied to the implantable device by an external instrument such as Magnetic Resonance Imaging (MRI) or electromagnetic interference (EMI).

One feature of the present invention is to provide the isolation system with a magnetic insulator arranged to cover at least a portion of the pulse generator, lead, and electrode, and to shield this portion at least substantially from the magnetic field and RF signal. This insulating system minimizes the formation of the induction loop through the shielded portion, and further minimizes the flow of the induction current through the induction loop to the patient's heart. The magnetic insulation of the isolation system is permanent and it shields the implanted device from the magnetic field and RF signals. It is understood, however, that there may be some flow of the induction current through the induction loop, although it may have a very low amplitude.

Another feature of the present invention is to provide the dynamic isolation system with a sensor unit, a switch bank, and a controller. The sensor unit is configured to sense the intensities of an external magnetic fields and/or a RF signal. The switch bank includes at least one switch, and the controller is configured to be operatively coupled to the sensor unit, to receive the sensed intensities therefrom, and to compare the sensed intensities to preset limits. The controller is also configured to be operatively coupled to the switch bank, to close the switch of the switch bank in a normal operation mode where the sensed intensities are less than the limits, and to open the switch in an isolation mode where the intensities exceed the limits, thereby eliminating the formation of the induction loop through the lead and minimizing flow of induction current through the induction loop to the patient's heart.

Advantageously, the dynamic isolation system can electrically isolate selected parts of the implantable device only when the device is subjected to the external magnetic field and/or RF signal. Accordingly, the isolation system can eliminate the induction loops formed between various parts of the implantable device and the tissues of the patient's heart, thereby avoiding the induction current from flowing therethrough. More advantageously, the dynamic isolation system can cause the implantable device to resume its normal function whenever the magnetic field and/or RF signal disappear or their intensities fall below the preset limits.

More particularly, the sensor unit includes at least one magnetic field sensor and at least one RF sensor that may be a regular untuned RF sensor, a tuned RF sensor arranged to sense the RF signal with a specific frequency, a tunable RF sensor, or a like sensor. The tunable RF sensor may include a swept RF detector with at least one voltage variable capacitor and at least one planar spiral inductor to sense the RF signals having different frequencies.

In one embodiment, the tunable RF sensor includes a digitally selectable set of inductors and/or capacitors, so that the tunable RF sensor may be tuned to RF signals with multiple preselected frequencies to sense RF signals at those frequencies. The tunable RF sensor may be a capacitor-tuned RF sensor including multiple inductive antennas arranged in different directions, such as three inductive antennas arranged in three mutually orthogonal axes. Each of these inductive antennas includes multiple capacitors connected in series and multiple switches disposed between the capacitors. The switches are arranged to open and close the capacitors to tune the RF sensor to the RF signals at different frequencies. Either the magnetic field and RF sensor may be disposed in a suitable location relative to the implantable device, such as on the outer case, in the generator case, or in the header which is a connection mechanism that secures the leads to the generator.

The controller is arranged to open the switches when the intensity sensed by at least two sensors of different types, exceeds a preset limit for that intensity. When the intensity of the magnetic field exceeds the preset limit of the magnetic field, and when the intensity of the RF signal exceeds the present limit for the RF signal, thereby minimizing false detection of the presence of undesirable RF signal and/or magnetic field.

The controller may include at least one non-filtered feedthrough disposed around the lead forming a hermetic seal to the generator case and located between the electrode and the switch bank, in order to prevent the formation of a high frequency induction loop in the isolation mode. The controller may include at least one filtered feedthrough disposed along the lead and between the switch bank and pulse generator, so as to prevent potentially damaging high frequency signals from passing down the lead to the sensitive pulse generator circuitry.

The implantable device may include a sub-enclosure configured to include the non-filtered feedthrough and the switch bank at one of its ports and the filtered feedthrough at another port. The non-filtered feedthrough may be disposed around each lead or around multiple leads. The controller includes a switching unit configured to switch the dynamic isolation system out of the isolation mode to the normal mode, upon occurrence of at least one triggering event such as an elapse of a preset period, after the system is switched from the normal mode to the isolation mode.

Yet another feature of the present invention is to provide the attenuation system with at least a first magnetoresistor disposed in series with the feedthrough, in between the outer case and a junction along the lead. The first magnetoresistor is configured to have a relatively high resistance, and to attenuate the current induced by the external magnetic field and/or RF signals. Advantageously, the attenuation system can minimize the flow of the induction current through the induction loop, to the patient's heart, only when subjected to the external magnetic field. It is understood, however, that the flow of the induction current through the induction loop may be significantly attenuated or completely eliminated.

Still another feature of this invention is to provide a method of minimizing the flow of the induction current through the induction loop formed in the implantable device. Such a method comprises the steps of magnetically insulating at least a portion of the implantable device from the magnetic field and RF signal, and minimizing the induction current flowing through the induction loop to the patient's heart.

Another method is also provided for isolating at least one part of the device for minimizing formation of the induction loop in the implanted device through the isolated part of the implanted device. The method comprises the steps of sensing the intensity of the magnetic field and RF signal by means of a magnetic field sensor and a RF sensor, respectively; comparing the sensed intensities to corresponding preset limits; maintaining the implanted device in a normal operation mode when both the sensed intensities are less than the preset limits; and electrically isolating a part of the implanted device in an isolation mode when any one of the sensed intensity exceeds its preset limit, thereby minimizing the formation of the induction loop, and further reducing the flow of the induction current through the induction loop to the patient's heart. Alternatively, the system goes into an isolation mode when both RF and magnetic sensors are triggered.

Another feature of this invention is to provide a method of minimizing the flow of the induction current through the induction loop formed in the implantable device. This method comprises the steps of implementing at least one first magnetoresistor along the induction loop; subjecting the first magnetoresistor to the magnetic field; and increasing the resistance of the first magnetoresistor to attenuate the induction current through the induction loop.

Thus, the foregoing and other features of the present invention are realized by an implantable cardiac stimulation device equipped with an isolation system capable of minimizing induction currents flowing through the implantable devices or eliminating induction loops through which the induction current flow.

BRIEF DESCRIPTION OF THE DRAWINGS

Various features of the present invention and the manner of attaining them will now be described in greater detail with reference to the following description, claims, and drawings, wherein:

FIG. 3 is comprised of FIGS. 3A, 3B, 3C, and represents a schematic diagram of exemplary induction loops formed around selected parts of the implanted cardiac stimulation device and surrounding tissues according to the present invention, wherein

DETAILED DESCRIPTION

The following description is not to be taken in a limiting sense but is made merely for the purpose of describing the general principles of the invention. In the description of the invention that follows, like numerals or reference designators will be used to refer to like parts or elements throughout. The present invention is directed at providing various magnetic field detecting isolation systems for implantable cardiac stimulating devices with pacemaking, cardioversion, and/or defibrillation capabilities, and other stimulation devices such as neurological devices.

Figure 1:
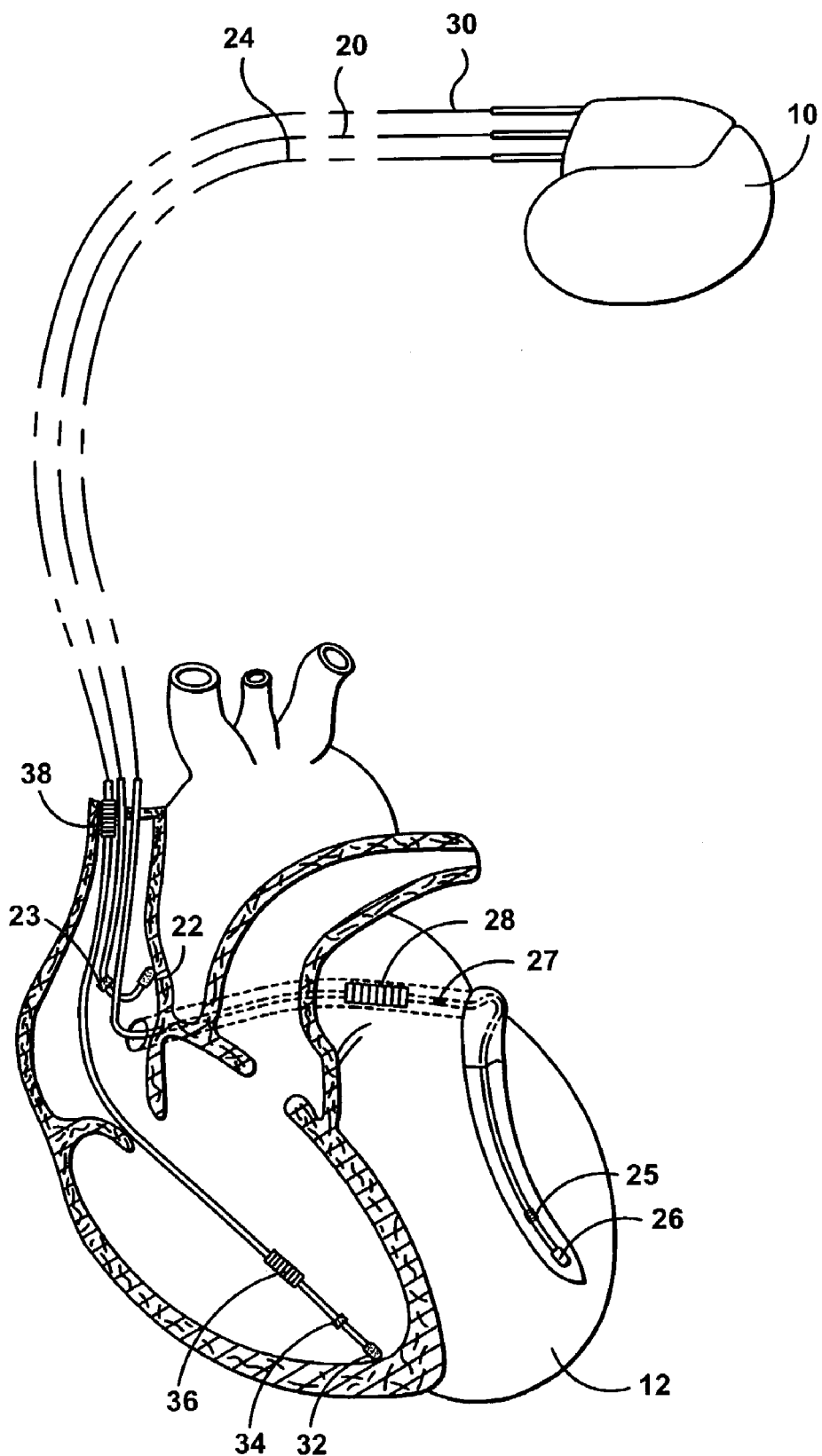
FIG. 1 is a simplified, partly cut-away view of an exemplary implantable cardiac stimulation device in electrical communication with at least three leads implanted into a patient's heart for delivering multi-chamber stimulation and shock therapy according to the present invention.
Figure 2:
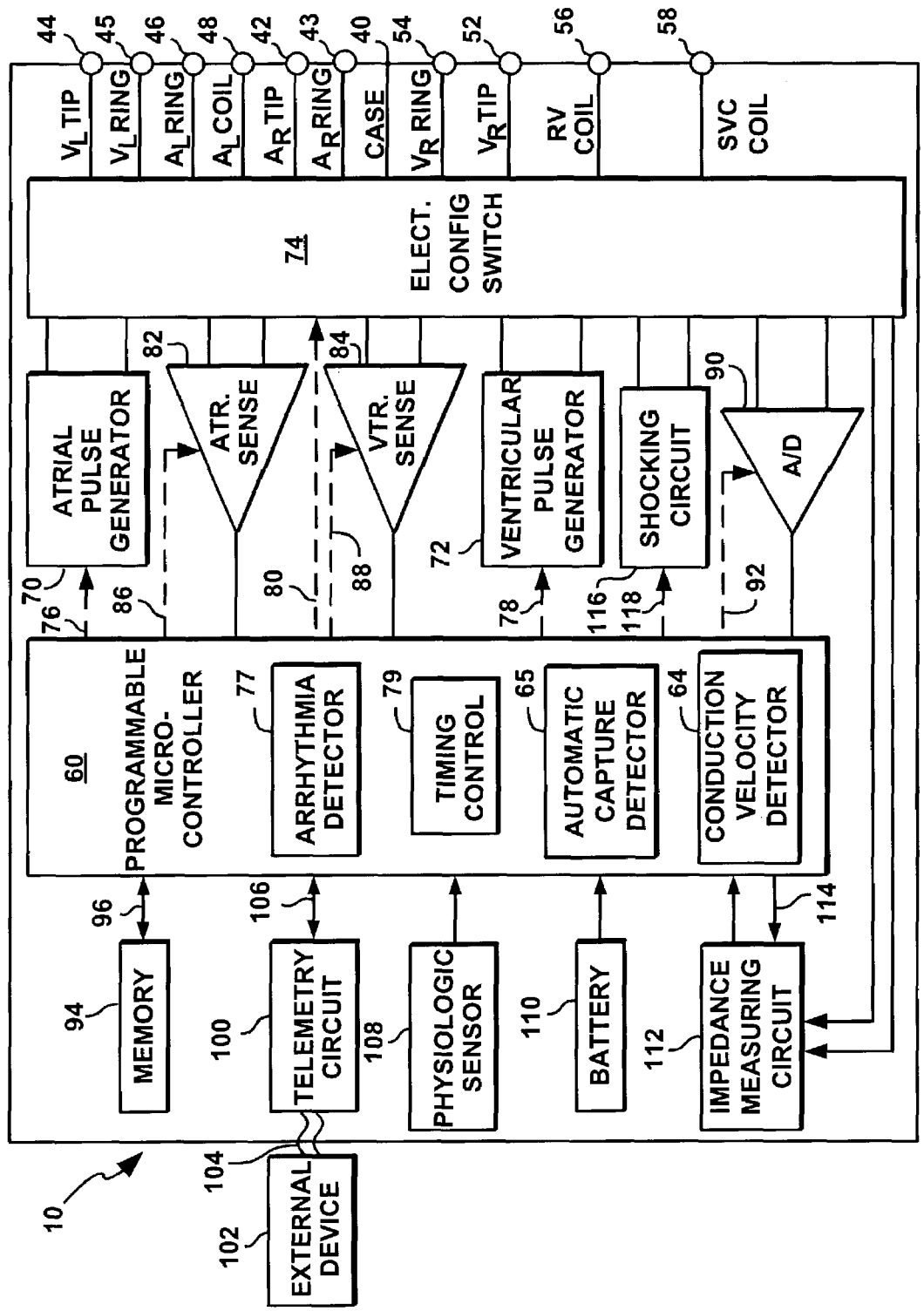
FIG. 2 is a functional block diagram of the exemplary implantable cardiac stimulation device of FIG. 1, illustrating the basic elements providing pacing stimulation, cardioversion, and defibrillation in four chambers of the heart according to the present invention.

A cardiac stimulation device will thus be described in conjunction with FIGS. 1 and 2, in which the features included in this invention could be implemented. It is recognized, however, that numerous variations of such a device exist in which various methods included in the present invention can be implemented without deviating from the scope of the present invention.

FIG. 1 illustrates a stimulation device 10 in electrical communication with a patient's heart 12 by way of three leads 20, 24 and 30 suitable for delivering multi-chamber stimulation and/or shock therapy. To sense atrial cardiac signals and to provide right atrial chamber stimulation therapy, the device 10 is coupled to an implantable right atrial lead 20 including at least one atrial tip electrode 22 that typically is implanted in the patient's right atrial appendage. The right atrial lead 20 may also include an atrial ring electrode 23 to allow bipolar stimulation or sensing in combination with the atrial tip electrode 22.

To sense the left atrial and left ventricular cardiac signals and to provide left-chamber stimulation therapy, the stimulation device 10 is coupled to a "coronary sinus" lead 24 designed for placement in the "coronary sinus region" via the coronary sinus ostium in order to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to: receive atrial and/or ventricular cardiac signals; deliver left ventricular pacing therapy using at least one left ventricular tip electrode 26 for unipolar configurations or in combination with left ventricular ring electrode 25 for bipolar configurations; deliver left atrial pacing therapy using at least one left atrial ring electrode 27 as well as shocking therapy using at least one left atrial coil electrode 28.

The stimulation device 10 is also shown in electrical communication with the patient's heart 12 by way of an implantable right ventricular lead 30 including, in this embodiment, a right ventricular (RV) tip electrode 32, a right ventricular ring electrode 34, a right ventricular coil electrode 36, a superior vena cava (SVC) coil electrode 38, and so on. Typically, the right ventricular lead 30 is inserted transvenously into the heart 12 so as to place the right ventricular tip electrode 32 in the right ventricular apex such that the RV coil electrode 36 is positioned in the right ventricle and the SVC coil electrode 38 will be positioned in the right atrium and/or superior vena cava. Accordingly, the right ventricular lead 30 is capable of receiving cardiac signals, and delivering stimulation in the form of pacing and shock therapy to the right ventricle.

FIG. 2 illustrates a simplified block diagram of the multi-chamber implantable stimulation device 10, which is capable of treating both fast arrhythmia and slow arrhythmia with stimulation therapy, including cardioversion, defibrillation, and pacing stimulation. While a particular multi-chamber device is shown, this is for illustration purposes only, and one of ordinary skill in the pertinent art could readily duplicate, eliminate or disable the appropriate circuitry in any desired combination to provide a device capable of treating the appropriate chamber(s) with cardioversion, defibrillation, and/or pacing stimulation.

The stimulation device 10 includes a housing 40 which is often referred to as "can," "case," or "case electrode," and which may be programmably selected to act as the return electrode for all "unipolar" modes. The housing 40 may further be used as a return electrode alone or in combination with one or more of the coil electrodes 28, 36, or 38, for defibrillation shocking purposes.

Figure 7:
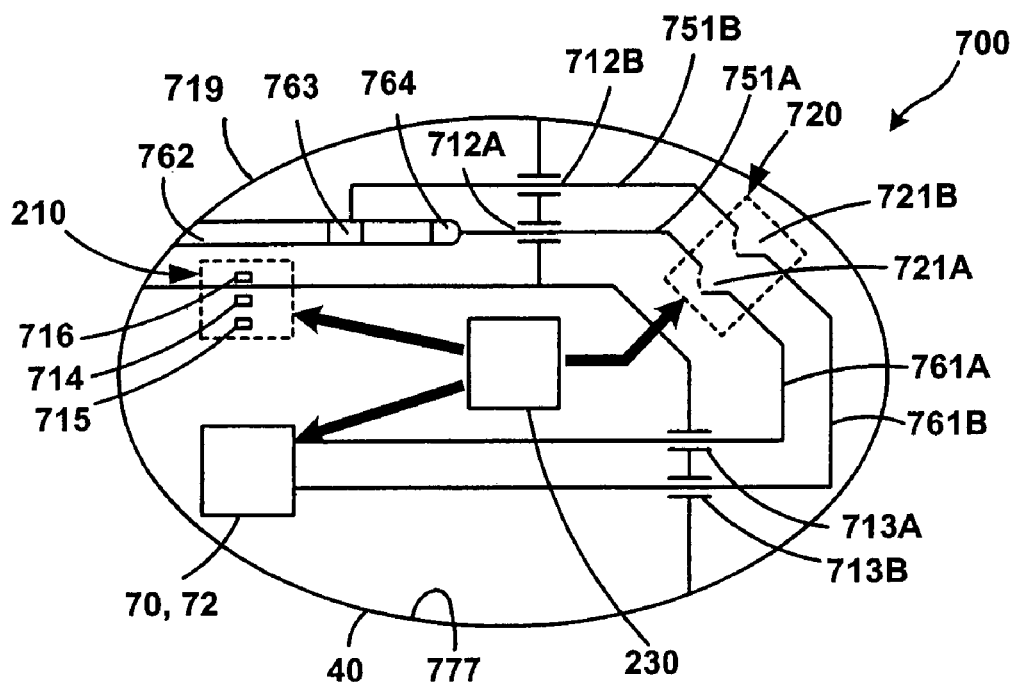
FIG. 7 is a circuit diagram of an exemplary dynamic isolation system of the present invention for use with a single bipolar lead.
Figure 8:
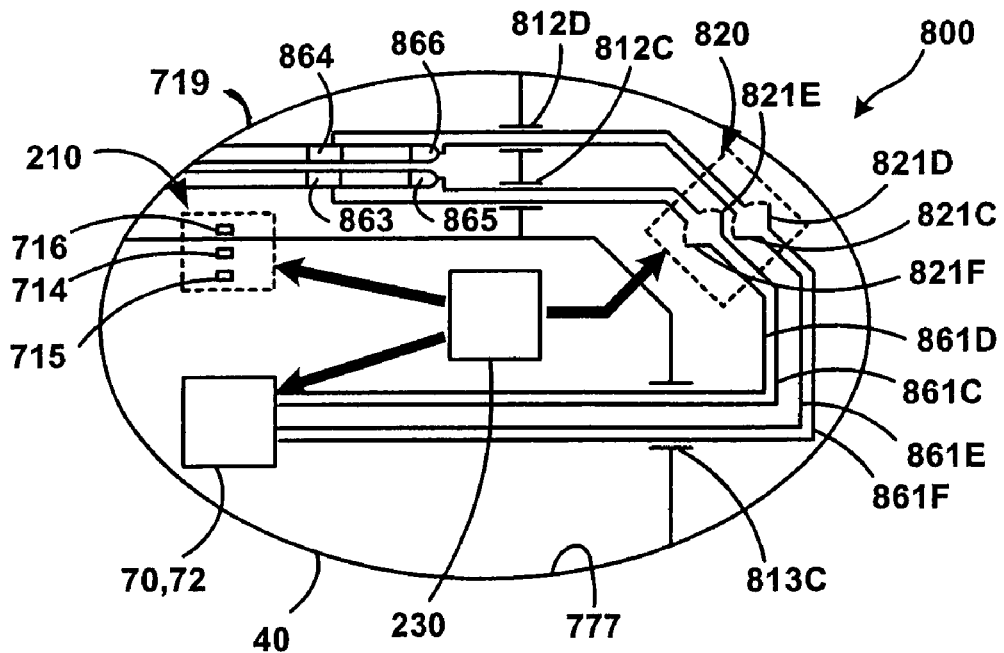
FIG. 8 is a circuit diagram of another exemplary dynamic isolation system of the present invention for use an implantable stimulation device with dual bipolar leads.

With reference to FIGS. 7 and 8, the stimulation device 10 is generally comprised of a header 719, and a sealed compartment 777 that houses the internal circuitry and switch bank of the device 10. In a preferred embodiment, the header 719 is made of a dielectric material, and the sealed compartment 777 is made of an electrically conductive material and is referred to as the housing or case 40.

The housing 40 further includes a connector having a plurality of terminals 42, 43, 44, 45, 46, 48, 52, 54, 56, and 58 (shown schematically and, for convenience, the names of the electrodes to which they are connected are shown next to corresponding terminals). As such, in order to achieve right atrial sensing and stimulation, the connector includes at least one right atrial tip terminal ($A_R$ TIP) 42 adapted for connection to the atrial tip electrode 22. The connector may also include a right atrial ring terminal ($A_R$ RING) 43 for connection to the right atrial ring electrode 23.

To achieve left chamber sensing, pacing, and/or shocking, such a connector includes a left ventricular tip terminal ($V_L$ TIP) 44, a left ventricular ring terminal ($V_L$ RING) 45, a left atrial ring terminal (AL RING) 46, and a left atrial shocking coil terminal (AL COIL) 48, that are adapted for connection to the left ventricular tip electrode 26, the left ventricular ring electrode 25, the left atrial ring electrode 27, and the left atrial coil electrode 28, respectively.

To support right ventricular sensing, pacing, and/or shocking, the connector may further include a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular (RV) tip electrode 32, the RV ring electrode 34, the RV coil electrode 36, and the SVC coil electrode 38, respectively.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may include RAM or ROM memory, logic and timing circuitry, state machine circuitry, and/or I/O circuitry. Typically, the microcontroller 60 may have the ability to process or monitor various input signals (data) as controlled by a program code stored in a designated block of memory.

FIG. 2 illustrates an atrial pulse generator 70 and ventricular pulse generator 72 which generate stimulation pulses for delivery by the right atrial lead 20, the right ventricular lead 30, and/or the coronary sinus lead 24 via a switch 74. It is understood that, to provide the stimulation therapy in each of the four chambers of the heart, the atrial pulse generator 70 and the ventricular pulse generator 72 may include, e.g., dedicated pulse generators, independent pulse generators, multiplexed pulse generators, and/or shared pulse generators. The atrial pulse generator 70 and the ventricular pulse generator 72 are generally controlled by the microcontroller 60 via appropriate control signals 76 and 78, respectively, to trigger or inhibit the stimulation pulses.

The microcontroller 60 may further include timing control circuitry 79 which may be used to control timing of the stimulation pulses such as, e.g., pacing rate, atrio-ventricular (AV) delay, atrial interchamber (A—A) delay, and/or ventricular interchamber (V—V) delay. Such timing control circuitry 79 may also be used to keep track of the timing of refractory periods, noise detection windows, evoked response windows, alert intervals, marker channel timing, and so on.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, and the like) by selectively closing the appropriate combination of switches. Atrial sensing circuits 82 and ventricular sensing circuits 84 may also be selectively coupled to the right atrial lead 20, coronary sinus lead 24, and the right ventricular lead 30 through the switch 74, for detecting the presence of cardiac activity in each of the four chambers of the heart.

Accordingly, the atrial sensing circuit 82 and the ventricular sensing circuit 84 may include dedicated sense amplifiers, multiplexed amplifiers or shared amplifiers. The switch 74 determines the "sensing polarity" of the cardiac signal by selectively closing the appropriate switches. In this way, the clinician may program the sensing polarity independent of the stimulation polarity.

Each of the atrial and ventricular sensing circuits 82, 84 preferably employs one or more low power, precision amplifiers with programmable gain, automatic gain or sensitivity control, band-pass filtering, and threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation.

The outputs of the atrial sensing circuit 82 and ventricular sensing circuits 84 may be connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, may receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

For arrhythmia detection, the stimulation device 10 includes an arrhythmia detector 77 that utilizes the atrial and ventricular sensing circuits 82 and 84 to sense cardiac signals, for determining whether a rhythm may be physiologic or pathologic. As used herein, "sensing" generally refers to the process of noting an electrical signal, while "detection" generally refers to the step of confirming the sensed electrical signal as the signal being sought by the detector. As an example, "detection" applies to the detection of both proper rhythms (i.e., "P wave" or "R wave") as well as improper dysrhythmias including arrhythmia and bradycardia (e.g., detection of the absence of a proper rhythm).

The timing intervals between sensed events (e.g., P-waves, R-waves, and depolarization signals associated with fibrillation which are sometimes referred to as "F-waves" or "Fib-waves") are then classified by the arrhythmia detector 77 by comparing them to a predefined rate zone limit (e.g., bradycardia, normal, low rate ventricular tachycardia, high rate ventricular tachycardia, fibrillation rate zones, and so on) and various other characteristics (e.g., sudden onset, stability, physiologic sensors, morphology, and so on), in order to determine the type of remedial therapy required (e.g., bradycardia pacing, anti-tachycardia stimulation, cardioversion shocks or defibrillation shocks, collectively referred to as "tiered therapy").

Cardiac signals are also applied to the inputs of a data acquisition system 90 which is depicted as an analog-to-digital (A/D) converter for simplicity of illustration. The data acquisition system 90 is configured to acquire intracardiac electrogram (EGM) signals, convert the raw analog data into digital signals, and store the digital signals for later processing and/or telemetric transmission to an external device 102. Such a data acquisition system 90 may be coupled to the right atrial lead 20, the coronary sinus lead 24, and the right ventricular lead 30 through the switch 74 to sample the cardiac signals across any pair of desired electrodes.

Advantageously, such a data acquisition system 90 may be coupled to the microcontroller 60 and/or another detection circuitry, for detecting an evoked response from the heart 12 in response to an applied stimulus, thereby aiding in the detection of "capture." In the embodiment of FIG. 2, the microcontroller 60 may include an automatic capture detector 65 which searches for an evoked response signal following a stimulation pulse during a "detection window" set by timing control circuitry 79. The microcontroller 60 enables the data acquisition system 90 via control signal 92 to sample the cardiac signal which falls in the capture detection window. The sampled signal is evaluated by the automatic capture detector 65 to determine if it is an evoked response signal based on its amplitude, peak slope, morphology or another signal feature or combination of the features. Detecting the evoked response during the detection window may indicate that capture has occurred.

The microcontroller 60 may further be coupled to a memory 94 by a suitable data/address bus 96, wherein the programmable operating parameters used by the microcontroller 60 are stored and modified, as required, so as to customize the operation of the stimulation device 10 to suit the needs of particular patients. Such operating parameters may define, e.g., stimulation pulse amplitude, pulse duration, polarity of electrodes, rate, sensitivity, automatic features, arrhythmia detection criteria, and/or the amplitude, shape of waves, and/or vector of each stimulation pulse to be delivered to the patient's heart 12 within each respective tier of therapy.

The stimulation device 10 may additionally include a power source that may be illustrated as a battery 110 for providing operating power to all the circuits of FIG. 2. For the stimulation device 10 employing shocking therapy, the battery 110 must be capable of operating at low current drains for long periods of time, preferably less than 10 μA, and also be capable of providing high-current pulses when the patient requires a shock pulse, preferably in excess of 2 A, at voltages above 2 V, for periods of 10 seconds or more.

According to a preferred embodiment of the present invention, an implantable cardiac stimulation device 10, systems such as an ICD, is provided with a static isolation system and/or a dynamic isolation systems that are capable of preventing, or at least minimizing the formation of device-patient induction loops, and the like. The isolation system advantageously insulates various parts of the implantable device 10 that are susceptible to form induction loops when subjected to external electromagnetic fields, thereby eliminating or interrupting such induction loops.

Figure 3A:
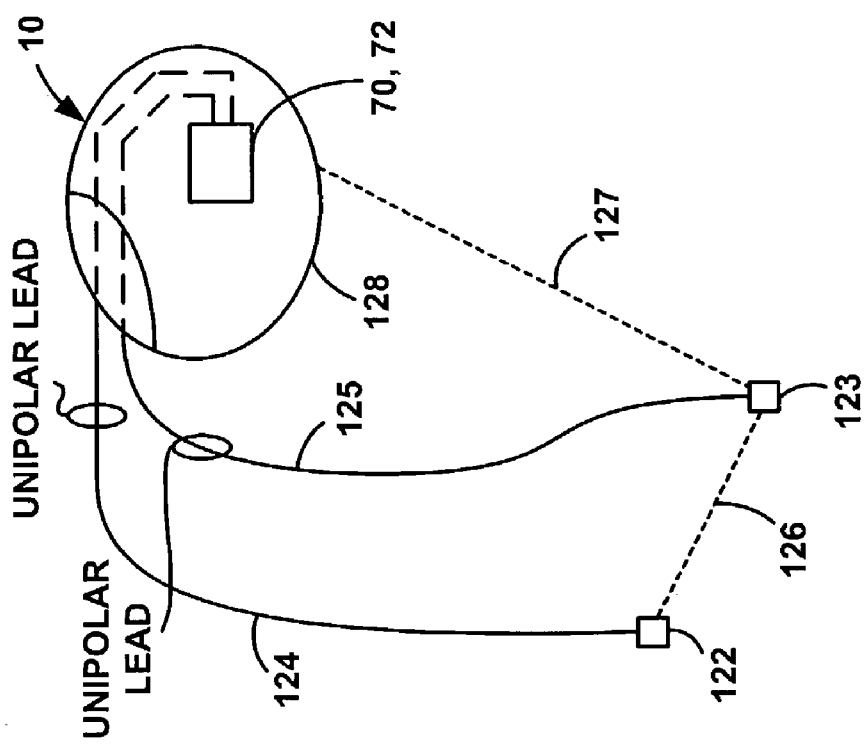
FIGS. 3A and 3B illustrate lead induction loops.
Figure 3B:
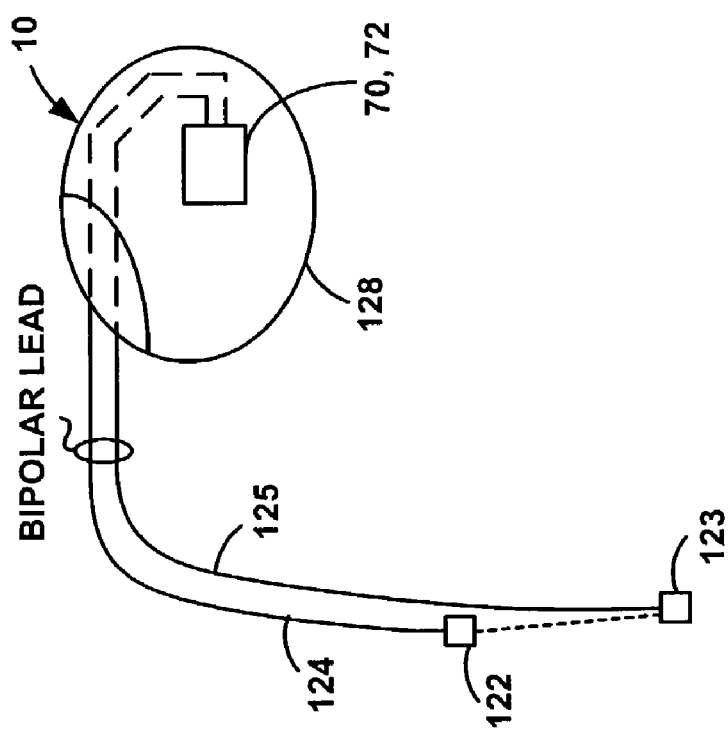
Figure 3C:
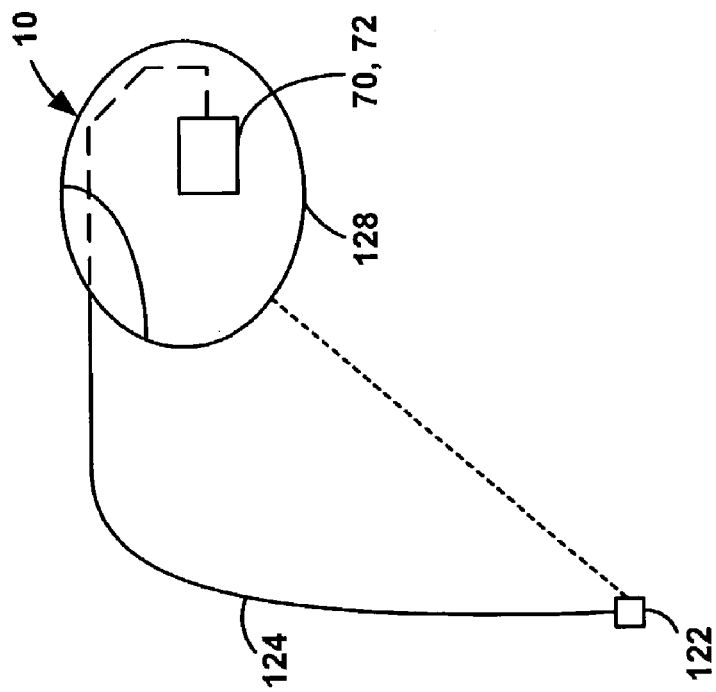
FIG. 3C illustrates a full system induction loop.

FIG. 3 (FIGS. 3A, 3B, 3C) shows exemplary induction loops that can be formed in or around the implanted ICD. FIG. 4 through FIG. 10 show various exemplary embodiments of the isolation system of the present invention that eliminate or interrupt the induction loops. It is recognized, however, that numerous variations of the disclosed system may also be practiced without deviating from the scope of the present invention. In another embodiment, the current loop does not pass through the pulse generators (70, 72) as it can pass across a filtered feedthrough of a conventional design to the case where it then finishes the loop through any of the other conductive paths.

With reference to FIG. 3A, when the stimulation device 10 is subjected to steady and/or unsteady external electromagnetic fields, various components of the stimulation device 10 and/or surrounding tissues may form unfavorable induction loops. More particularly, when the implanted stimulation device 10 is subjected to a magnetic field generated by, for example, an MRI system, or an EMI system, a voltage gradient may develop across different components of the stimulation device 10. As a result, an electric current may flow through induction loops that are comprised, for example, of pulse generators or case 70, 72, 40, electrodes 122 (i.e., tip or ring electrode), 123 (i.e., tip or ring electrode), leads 124, 125, and surrounding tissues 126, 127.

In the illustration of FIG. 3A, the induction current may flow from the pulse generators 70, 72, or case 40 to the electrode 123 through the lead 125. Due to the voltage gradient developed between adjacent electrodes 122, 123, the conductive tissues 126 may pass the induction current to the adjacent electrode 122. The induction current then returns to the pulse generators 70, 72, or case 40 through the lead 124, thereby completing a "device-tissue" loop or, more particularly, a "lead" induction loop 70 comprised of the following paths: 70 (or 72)-125-123-126-122-124-70 (or 72 or 40).

In addition, the induction current may flow from the pulse generators 70, 72, or case 40 to the electrode 123 through the lead 125, and return to the pulse generators 70, 72 directly along a return path comprised of the conductive tissues 127, thereby completing another "device-tissue," or "full system" induction loop that includes the following paths: 70 (or 72, 40)-125-123-127-70 (or 72, 40). Other paths may also be used, such as: 70 (or 72, 40)-125-123-127-70 (or 72, 40).

While FIG. 3A illustrates a lead induction loop created by two separate unipolar (or bipolar) leads, FIG. 3B illustrates a bipolar lead configuration with the induction loop created with one lead, i.e., 30, by the two lead conductors 124, 125, as follows: 70 (or 72 or 40)-125-123 (tip electrode)-122 (ring electrode)-124-70 (or 72 or 40). FIG. 3C illustrates a system induction loop created by the pulse generators 70, 72, or case 40, lead 124, and (tip or ring) electrode 122.

Moreover, the stimulation device 10 may also form "intradevice" induction loops that may connect various components of the stimulation device 10, such as the pulse generators 70, 72 and the housing 40 of the stimulation device 10, thus forming, for example an intradevice loop along the following paths: 70 (or 72)-40-70 (or 72). Depending upon the configuration of the electrodes, i.e., unipolar, bipolar, or multipolar, detailed electrical configurations of the stimulation device 10, and anatomy of the implant locations, numerous variations of the isolation system may be practiced without departing from the scope of the present invention.

The present invention provides an isolation system capable of insulating or isolating the aforementioned "device-tissue" and "intradevice" induction loops, and eliminating or interrupting the induction currents therealong. The isolation system may be generally classified into three general, non-exclusive, categories: a static isolation system, a dynamic isolation system, and a hybrid system.

The static isolation system includes one or more insulators disposed around selected parts or components of the stimulation device 10, and continuously shield such parts from external magnetic fields. The dynamic isolation system includes switch banks arranged to electrically isolate one or more selected components of the stimulation device 10 when the external magnetic field exceeds a preset limit.

Figure 4:
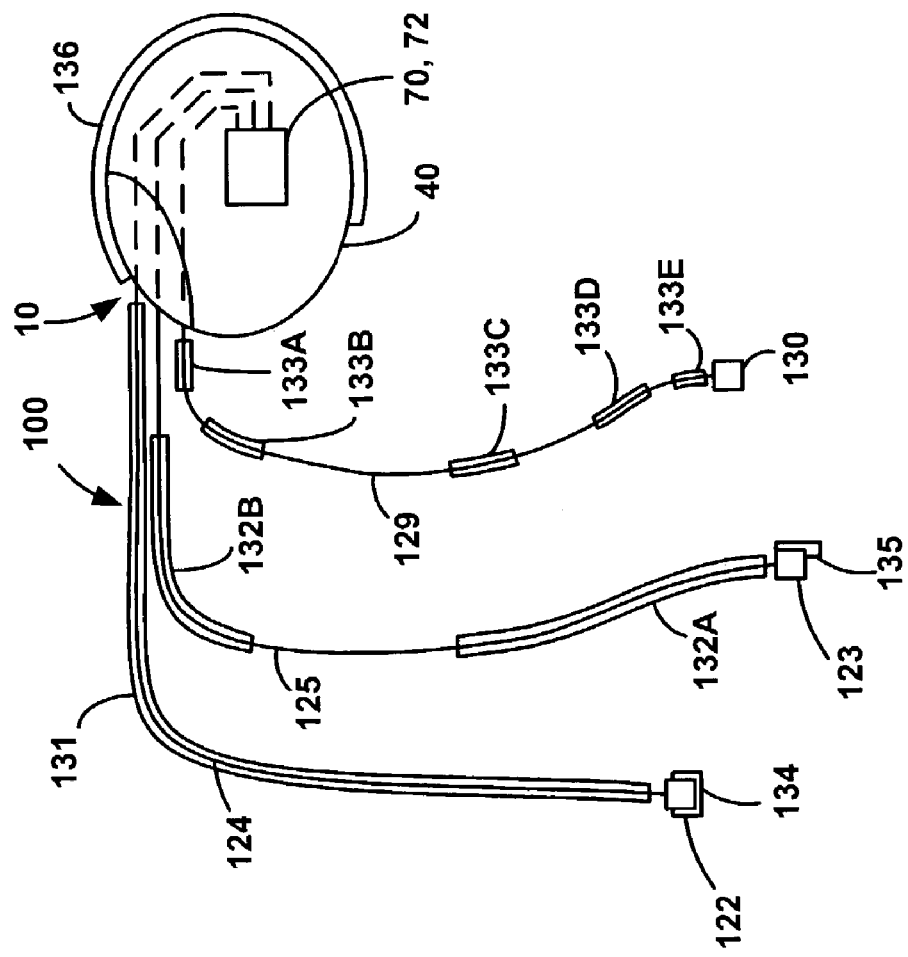
FIG. 4 is a schematic diagram of an exemplary static isolation system for insulating selected parts of the implanted cardiac stimulation device according to the present invention.

In one aspect of the present invention, a plurality of static isolation systems may be provided to magnetically insulate at least some of the components of the stimulation device 10 that form the device-tissue and intradevice induction loops, thereby eliminating or disrupting the induction loops. FIG. 4 illustrates a schematic diagram of one such static isolation system.

The static isolation system 100 is comprised of a plurality of magnetic insulators capable of magnetically shielding components from an external magnetic field. These insulators may be disposed at desired locations of the stimulation device 10. As an example, a magnetic insulator 131 is configured to cover a substantial portion of, or to entirely cover the implanted lead 124. Magnetic insulators 132A, 132B have lengths that are shorter than that of the lead 125 to cover selected segments of the lead 125.

In the alternative, much shorter magnetic insulators 133A–133E may be disposed along the electrode lead 129, at, for example, equidistal or different distances. These magnetic insulators 131, 132A, 132B, and 133A-133E may shield the entire or selected portions of the leads 124, 125, 129 from magnetic fields generated by MRI or EMI systems, thereby constantly eliminating or interrupting the formation of the induction loops as explained earlier.

The foregoing magnetic insulators 131, 132A, 132B, and 133A–133E of the static isolation system 100 may generally be coated or otherwise coupled to the electrode leads 124, 125,129. In the alternative, the magnetic insulators 131, 132A, 132B, and 133A–133E may be concentrically wrapped around the leads 124, 125, 129, and optionally provided in multiple layers having different thicknesses and magnetic or similar properties. The thickness of these concentric magnetic insulators may be selected based on various factors such as the intensity of the magnetic fields, the magnetic insulation capacity, flexibility of the lead, biocompatibility, and abrasion resistance. In general, thicker magnetic insulators shield stronger magnetic fields. However, the magnetic insulators are generally designed to have an optimal thickness to optimize the insulation while retaining the requisite flexibility of the leads for easier handling and implantation.

Other components of the implanted cardiac stimulation device 10 may also be shielded. For example, magnetic insulators 134 and 135 may partially or entire enclose the electrodes 122 and 123, respectively. The housing 40 of the stimulation device 10 may be completely or partially enclosed and shielded by another magnetic insulator 136.

In addition, various parts or components within the housing 40 can be selectively shielded. As an example, magnetic insulators may enclose the housing (not shown) of the pulse generators 70, 72 to eliminate generator-lead-tissue induction loops and to attenuate the intensity of any induction current to the pulse generators 70, 72.

These magnetic insulators may generally be made of, or may include various insulating materials such as parylene (paraxylylene) conformal coating. The magnetic insulators may be configured to be highly insulative and to block passage of both large and small induction currents. In the alternative, the insulators may be made only partially insulative so that only large currents can pass through. Although these embodiments may be effective to eliminate induction loops, it may be desirable to have such induction current loops available for unipolar operation as the housing is the required return path.

In another aspect of this invention, various dynamic isolation systems are provided to electrically insulate selected components or parts of the implanted cardiac stimulation device 10, to prevent or at least to minimize the "device-tissue" and/or "intradevice" induction loops, when the strength of the magnetic field exceeds a preset limit. These dynamic isolation systems do not provide insulation or isolation during the normal operation of the implanted device 10. Various embodiments of the dynamic isolation systems will now be described in conjunction with FIGS. 5 through 9.

Figure 5:
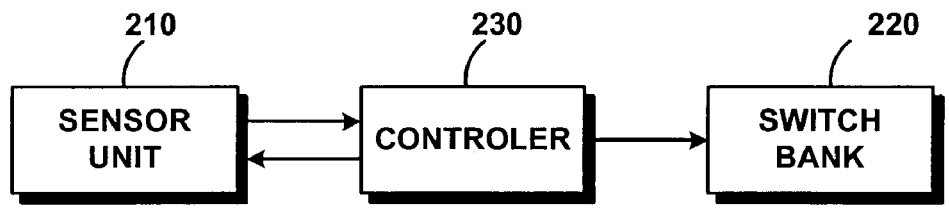
FIG. 5 is a block diagram of an exemplary dynamic isolation system for isolating various parts of the implanted cardiac stimulation device according to the present invention.

FIG. 5 is a high level block diagram of an exemplary dynamic isolation system 200 that insulates or isolates selected components of the stimulation device 10. The dynamic isolation system 200 comprises a sensor unit 210, a switch bank 220 (720 in FIG. 7 or 820 in FIG. 8), and the microcontroller 60 (also interchangeably referred to herein as controller 230).

The sensor unit 210 includes various sensors such as magnetic field sensors and radio-frequency (RF) sensors, to monitor the presence of magnetic fields or RF signals, the strengths of detected magnetic fields and/or RF signals, and the frequencies, amplitudes, or other wave characteristics of the RF signals.

The switch bank 220 (720 in FIG. 7 or 820 in FIG. 8) comprises multiple switches disposed between different components of the device 10, such as the pulse generators 70, 72, the electrodes 122, 123, 130, and the leads 124, 125, 129.

The controller 230 is operatively coupled to the sensor unit 210 and the switch bank 220 (720 or 820), and receives the signal from the sensor unit 210. The controller 230 regulates the operation of the switches of the switch bank 220 (720 or 820) based on the detected magnetic fields and/or RF signals.

In operation, the magnetic field sensors and RF sensors of the sensor unit 210 monitor the presence and intensities of the external magnetic fields and/or RF signals, and transmit the corresponding analog or digital signals to the controller 230. In turn, the controller 230 determines whether the measured intensities of the magnetic fields and/or the RF signals exceed preset limits, and if so, the controller 230 actuates the switches of the switch bank 220 (720 or 820) to open or close selected circuits, in order to eliminate or disrupt induction loops that would otherwise be formed to conduct induction current therethrough. After a preset period of time, or after the magnetic fields or RF signals have disappeared or faded below their respective preset limits, the controller 230 resets the switches so that the stimulation device 10 can resume its normal operation.

The controller 230 may also be configured to compare the voltage and/or current measured by the optional voltage and/or current sensors of the sensor unit 210 to normal operating values or ranges. If the measured voltage or current exceeds its preset value, or if it falls outside a preset range, the controller 230 regulates the switches of the switch bank 220 (720 or 820) to actuate/open the circuit that would otherwise form the induction loops.

Any appropriate magnetic sensor may be used as the magnetic field sensor of the sensor unit 210 as long as such sensor is capable of verifying whether the stimulation device 10 is in a magnetic field environment (e.g., MRI and EMI systems), and is further capable of sensing the strength of the magnetic field. Examples of this magnetic field sensors include magnetoresistors operating according to either the Gauss or Hall effect.

The magnetic field sensors can preferably measure a magnetic field with a strength ranging approximately between 0.01 tesla to 10 teslas. The magnetic field sensors are configured to sense the presence and intensity of steady and/or unsteady (i.e., changing over time) magnetic fields. Such magnetic field sensors may generally be disposed inside or outside the housing 40 of the device 10.

The magnetoresistors of the magnetic field sensor generally refer to magnetically influenced resistors that are made, for example, of InSb/NiSb, and that operate according to the Gauss effect. As opposed to the Hall generators, the InSb crystal has needles of low resistive NiSb alloyed thereinto.

The magnetoresistors maintain an equal distribution of the charge carriers throughout their cross-sections.

The lengthening of the paths of the charge carriers with increasing magnetic field increases the resistance of the magnetoresistors independent of the polarity of the induction. An example of such a magnetoresistor is Infineon OHAX0121 which is the D-type InSb/NiSb. The magnetic field sensors may further be implemented into the switches of the switch bank 220 (720 or 820) to form magnetic field-sensitive switches.

The RF sensors of the sensor unit 210 may be either frequency-specific RF sensors (i.e., tuned RF sensors) or generic RF sensors. Both RF sensor types are configured to sense RF signals such as the image signals for the MRI systems in the RF ranges, RF signals from the EMI systems, noise from such systems, and other signals or noises from various equipment capable of generating magnetic fields therearound.

In an exemplary embodiment, the tuned RF sensor may be set for a predetermined frequency of a particular MRI system to detect the RF signals of this MRI system. In another embodiment, the RF sensor may be a varactor-tuned inductor configured to sense the RF signals with different frequencies by varying the DC voltage applied thereto. In yet another embodiment, the RF sensor may be set for multiple frequencies and configured to be switched or tuned to sense RF signals having a desirable frequency.

Figure 6:
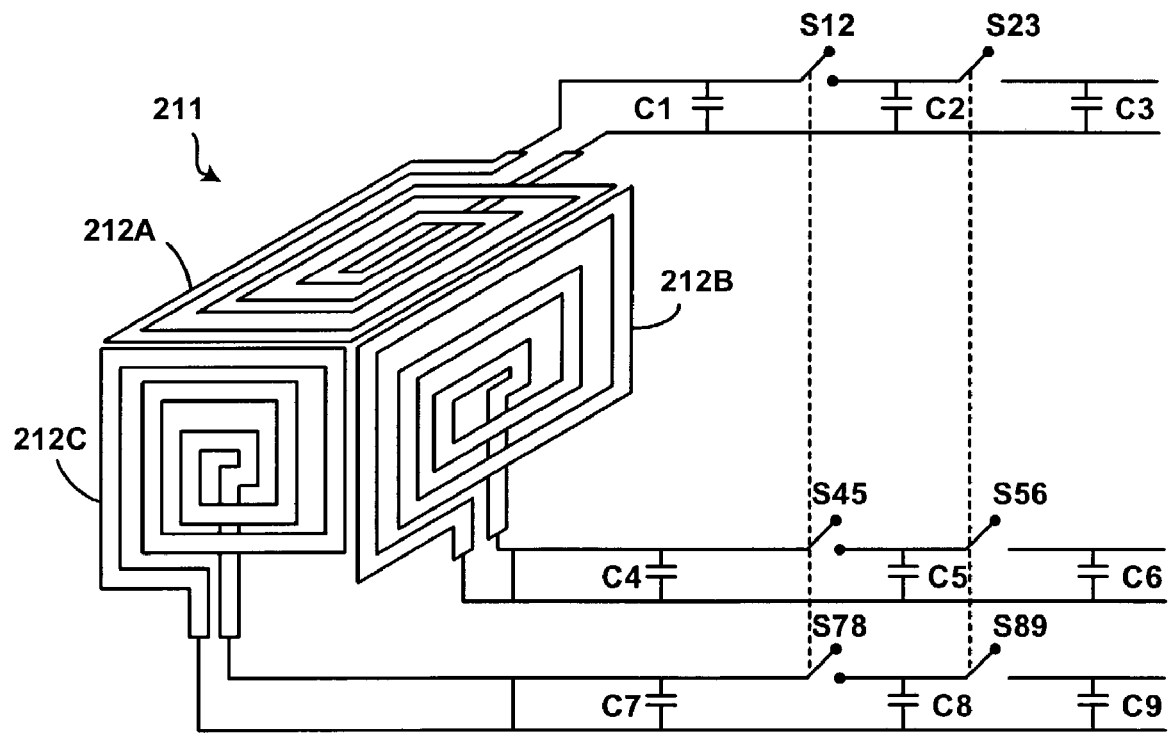
FIG. 6 is a circuit diagram of an exemplary capacitor-tuned RF sensor according to the present invention for use in triggering one embodiment of the dynamic isolation system of FIG. 5.

An exemplary tunable RF sensor 211 is illustrated in FIG. 6 which is a schematic diagram of an exemplary capacitor-tuned RF sensor according to the present invention. The RF sensor 211 includes a plurality of (i.e., three) inductive antennas or loops 212A, 212B, and 212C, each of which is connected to a plurality of (i.e., three) tuning capacitors C1–C3, C4–C6, and C7–C9, as well as a plurality of (i.e., two) switches S12–S23, S45–S56, and S78–S79, respectively.

In this particular example, the first inductive antenna 212A is connected to three capacitors C1, C2, C3 that are connected in parallel; switch S12 is connected in series between capacitors C1 and C2; and switch S23 is connected in series between capacitors C2 and C3. The second inductive antenna 212B is connected to three capacitors C4, C5, C6 that are connected in parallel; switch S45 is connected in series between capacitors C4 and C5; and switch S56 is connected in series between capacitors C5 and C6. The third inductive antenna 212C is connected to three capacitors C7, C8, C9 that are connected in parallel; switch S78 is connected in series between capacitors C7 and C8; and switch S89 is connected in series between capacitors C8 and C9.

The three antennas 212A, 212B, 212C of the RF sensor 211 are desirably oriented in three different directions or, preferably, in three mutually orthogonal directions, to detect RF signals propagating in all possible directions. Such configuration generally optimizes the sensitivity of the sensor 211. If desirable, the foregoing capacitor-tuned RF sensor 211 can also be embedded in an integrated circuit using conventional or available semiconductor fabrication techniques.

In operation, the capacitors will be switched to tune the RF sensor to the RF output of the MRI machine. Utilizing the equation $C=1/(4\pi^2 TLf^2)$, the capacitors are actively switched by the use of a programmer or automatically switched through the use of a phase-lock sensor.

Exemplary embodiments of dynamic isolation systems incorporating the foregoing sensors will now be described in conjunction with FIG. 7 and FIG. 8. FIG. 7 is a schematic diagram of a dynamic isolation system 700 that incorporates the sensor unit, the switch bank, the controller, filtered feedthroughs, and non-filtered feedthroughs in the stimulation device 10 configured to be coupled to a single bipolar lead according to the present invention. A feedthrough includes an insolated sealed passageway or access to the interior of the housing 40. When the feedthrough is capacitively coupled to the housing 40, it is referred to as a filtered feedthrough. When the feedthrough is not capacitively coupled to the housing 40, it is referred to as a non-filtered feedthrough. FIG. 8 is a schematic diagram of another exemplary dynamic isolation system 800 that incorporates the sensor unit, the switch bank, the controller, filtered feedthroughs, and non-filtered feedthroughs in the stimulation device 10 configured to be coupled to dual bipolar leads according to the present invention.

The dynamic isolation system 700 of FIG. 7 is comprised of the sensor unit 210, the switch bank 720, the controller 230, a plurality of non-filtered feedthroughs 712A and 712B, and a plurality of filtered feedthroughs 713A, 713B. The sensor unit 210 includes a magnetic field sensor 714 and a first RF sensor 715 that are disposed inside the housing 40 of the stimulation device 10. The sensor unit 210 further includes a second magnetic field and/or RF sensor 716 disposed inside the header 719 of the housing 40. The sensors of the sensor unit 210 may be selectively disposed at various locations relative to the housing 40. As an example, some of the sensors may be disposed inside the housing 40 or inside the can header 719; while others may be disposed outside the housing 40.

The exemplary sensors 714, 715, 716 of the sensor unit 210 detect the presence of an external magnetic field and/or an RF signal, continuously, intermittently, at pre-selected intervals, or upon the controller 230 receiving a command signal. The switch bank 720 is disposed within the sealed compartment 777 and its case 40, and includes two input/output switches 721A and 721B. The input/output switches 721A and 721B are disposed along the conduction paths that make contact with the external lead electrodes when the lead, such as lead 20, 24, or 30 (represented in FIG. 7 by the reference numeral 20) is connected to the stimulation device 10.

As described earlier, the controller 230 is operatively coupled to the sensor unit 210, and receives the sensed signals therefrom. The controller 230 is also operatively coupled to, and configured to control the switch bank 720 and the remaining components of the stimulation device 10, such as the pulse generators 70, 72.

The non-filtered feedthroughs 712A and 712B are disposed at the entry points of the conductors 751A, 751B into the sealed compartment 777, at the interface surface between the header 719 and the sealed compartment 777, and allow an unshielded magnetic interference, such as a magnetic field and/or an RF signal to actually enter the sealed compartment 777, thus preventing the formation of an induction loop between the case 40 of sealed compartment and the conductors 751A, 751B. The non-filtered feedthroughs 712A, 712B provide a hermetic seal through the housing 40 surrounding the internal input/output (I/O) leads (or insulated conductors) 751A and 751B. In addition to providing a hermetic seal for the I/O leads 751A, 751B at the points of entry into the sealed compartment 777, these non-filtered feed throughs 712A, 712B electrically isolate the I/O conductors 751A, 751B from the housing, preventing capacitive coupling or current flow between the housing and the I/O conductors that will occur at high frequencies if conventional filtered feedthroughs were used in a high frequency environment.

Filtered feedthroughs 713A, 713B are used to protect the internal circuitry of the stimulation device 10. The filtered feedthroughs 713A, 713B are disposed within the sealed compartment 777, and are capacitively coupled to the sealed compartment 777 case/housing 40 to protect the internal circuitry of the stimulation device 10. The filtered feedthroughs 713A, 713B are disposed between the switch bank and the internal circuitry such that when the switches 721A, 721B are opened, no current will flow to the housing 40, creating induction loops. When the switches 721A, 721B are closed, circuit damaging frequencies will be filtered to the housing 40, protecting the internal circuitry. The filtered feed throughs 713A, 713B are not required to be hermetically sealed as the non-filtered feed throughs 712A, 712B provide the sealed environment for the pulse generator.

In the embodiment of FIG. 7, the representative lead 20 includes a terminal 762 with two (or more) connectors 763, 764 that electrically connect the implanted electrodes, i.e., 22, 23 of lead 20 to the isolation system 700 and to the other components of the implanted stimulation device 10. More specifically, connector 763 is connected to switch 721B by means of a conductor 751B that extends through the non-filtered feedthrough 712B. In turn, switch 721B is connected to the atrial generator 70 by means of conductor 761B that extends through the filtered feedthrough 713B. Similarly, connector 764 is connected to switch 721A by means of a conductor 751A that extends through the non-filtered feedthrough 712A. In turn, switch 721A is connected to the atrial generator 70 by means of conductor 761A that extends through the filtered feedthrough 713A. It should be clear that while each of the conductors 751A, 751B, 761A, 761B is described as having its dedicated feedthrough 712A, 712B, 713A, 713B, respectively, some of these conductors could be arranged to share a single feedthrough.

The exemplary dynamic isolation system 800 of FIG. 8 is generally similar in design and function to the isolation system 700 of FIG. 7, except that the isolation system 800 is preferably used in a stimulation device 10 designed to be coupled with dual bipolar leads electrically connected to the internal I/O leads 861C, 861D, 861E, and 861F. In order to prevent or minimize induction currents through the internal leads 861C–861F, a pair of non-filtered feedthroughs 812C, 812D provide the hermetic seal through the housing 40 surround the internal input/output (I/O) leads 861C–861F. In addition to providing a hermetic seal for the I/O leads 861C–861F at the points of entry into the housing, these non-filtered feed throughs electrically isolated the I/O leads 861C–861F from the housing 40, preventing capacitive coupling or current flow between the housing and the I/O leads that will occur at high frequencies if conventional filtered feedthroughs are used in a high frequency environment.

A conventional filtered feedthrough 813C is used to protect the internal circuitry of the stimulation device 10. This filtered feedthrough is capacitively coupled to the housing 40 to protect the internal circuitry of the stimulation device 10. The filtered feedthrough 813C is located between the switch bank and the internal circuitry such that when the switches 821C, 821D, 821E, 821F are opened, no current flow to the housing 40, creating induction loops. When the switches 821C, 821D, 821E, 821F are closed, circuit damaging frequencies will be shunted to the housing 40 by the capacitively coupled feedthrough 813C, protecting the internal circuitry. The filtered feedthrough 813C is not required to be hermetically sealed as the non-filtered feed throughs 812C, 812D provide the sealed environment for the pulse generator.

In the embodiment of FIG. 8, each of the two (or more) input leads establishes a separate electrical conduction path that is similar to that described earlier in connection with lead 20 of FIG. 7.

In operation, the sensors 714–716 detect the presence of magnetic fields and/or RF signals and transmit the detected signals to controller 230, which in turn, compares these signals to their corresponding preset limits. When the detected signals exceed their limits, controller 230 activates (i.e., opens) switches 821C–821F of switch bank 820, to break the electrical conduction path of the I/O leads 861C–861F, thereby isolating the pulse generators 70, 72 and eliminating the induction loops which would otherwise pass the induction current through the filtered feedthrough 813C in a high frequency environment with steady or time-varying unsteady magnetic field.

More particularly, when a magnetic field or a RF signal is unsteady, the controller 230 may be configured to compare the measured average intensity of the magnetic field or RF signal to a preset average limit, or to compare the instantaneous maximum intensity of the magnetic field or the RF signal to a preset maximum limit. If the intensity of the magnetic field or RF signal falls below the preset limit, the controller 230 deactivates (i.e., closes) switches 821C–821F (i.e., "normal" mode) so that the stimulation device 10 can resume its normal operation. As it will be described below in greater detail, the controller 230 may also be configured to switch the stimulation device 10 from the isolation mode to the normal mode after a predetermined period of time, in order to prevent excessive or inappropriate inhibition of the normal operations (e.g., sensing, pacing, cardioversion, and defibrillation) of the stimulation device 10 during the isolation mode.

In order to optimize the elimination or interruption of the induction loops, the non-filtered feedthroughs 812C–812D and the I/O switches 821C–821F are preferably used. It is understood that the conventional filtered feedthrough 813 alone will allow high-frequency induction currents to flow thereacross to the housing 40, at high frequencies, thus creating induction loops. To prevent such high-frequency induction loops, the non-filtered feedthrough 812C–812D are preferably sealed hermetically and disposed intermediate the electrodes 863, 864, 865, 866 and the switches 821C–821F, so that they can prevent high-frequency induction currents from shunting conventional filtered feedthroughs to the case of the pulse generators 70, 72.

The feedthrough 813 is preferably disposed intermediate the internal switches 821C–821F and the pulse generators 70, 72, so that these switches 821C–821F prevent induction loops when the switches are activated (opened). Secondly, the filtered feedthrough 813C protects the circuitry from high frequencies when the switches 821C–821F are not activated (closed). In summary, the non-filtered feedthroughs 812C–812D and the switches 821C–821F can eliminate the induction current during the insulation (or isolation) mode (i.e., when the switches 821C–821F are open), while the filtered feedthrough 813 protects the pulse generator circuitry during the normal mode (i.e., when the switches 821C–821F are closed).

The foregoing tuned RF sensors 715–716 of the dynamic isolation system 800 are preferably disposed inside the housing 40 or may be located in the header 719 outside the housing 40. However, locating the RF sensors 715–716 inside the pulse generator housing 40 may have some disadvantages because the housing 40 of the pulse generators 70, 72 may shield the RF sensors 715–716 from external RF signals. This may prevent rapid detection of RF signals from an MRI machine or instrument emitting EMI. It being understood, however, that the RF sensor 716 is preferably disposed within the header 719 but outside the pulse generators housing 40 to optimize the detection sensitivity of the dynamic isolation system 800.

The accuracy in detecting the magnetic field and RF signal by the dynamic isolation system 800 may be improved by employing multiple sensors within sensor unit 210. In general, a more versatile sensing unit 210 (i.e., different types of sensors) will become more sensitive and more suitable to avoid inappropriate actuation of the switches 821C–821F that may result from false magnetic field detection or false RF signal detection.

In this regard, the sensor unit 210 preferably includes at least one magnetic field sensor and at least one tuned or regular RF sensor. The controller 230 for the sensor unit 210 is configured to activate the switches 821C–821F of the switching bank 820 (open the internal I/O leads 861C–861F) upon detection of preset triggering events. For example, the controller 230 may activate the switches 821C–821F in a logical "AND" configuration, that is when the magnetic field sensor 714 detects the presence of an undesirable magnetic field, and when at least one of RF sensors 715, 716 detects the presence of an undesirable RF signal. This combination can advantageously avoid, or at least minimize the inappropriate switching operations resulting from the false detection of the magnetic field or RF signal alone.

In the event that dynamic isolation switching is desired to protect against other forms of radio frequency EMI such as electronic security devices, electric article surveillance devices, and the like, the combinatorial logic required to activate switching can be adjusted to initiate switching for a wider range of sensing conditions.

In operation, the magnetic field sensor 714 senses the presence of a Telsa-level steady or unsteady magnetic field, and the RF sensors 715, 716 detect the presence of RF signals. The controller 230 receives the detected signals from these sensors, and compares them to preset limits for the magnetic field and/or RF signals.

When the sensed intensity of the magnetic field exceeds its preset limit for an allowable magnetic field strength, and when the intensity of the RF signals also exceeds its allowable RF signal intensity, the controller 230 activates or opens the switches 821C–821F of the switch bank 820 to eliminate or interrupt the induction currents. When the sensed signals indicate that the intensity of the magnetic field or RF signal falls below the preset limit, the controller 230 closes or deactivates switches 821C–821F so that the stimulation device 10 could resume its normal operation in a normal mode.

Numerous variations of the present systems and methods may exist without deviating from the scope of this invention. For example, the controller 230 may be configured to perform additional functions to improve accuracy in detecting the magnetic field and/or RF signal and to prevent or minimize false detection.

In one embodiment, a feedback mechanism such that the controller 230 receives the sensed signals from tunable sensors and controls at least some of the sensors based on the sensed signals in order to detect the presence and intensity of the external magnetic field and RF signal. Examples of such tunable sensors include, but are not limited to, analog RF sensors with tunable swept RF detectors including voltage-variable capacitors and planar spiral inductors, and digital RF sensors incorporating digitally selectable sets of capacitors and inductors for optimal selectivity of the preset sources of the RF signals.

In one embodiment of a tuned RF sensor, the sensor 715 or 716 may be adjusted to match the output of an MRI. If the magnetic field sensor 714 detects the presence of a high-telsa magnetic field, the controller 230 initiates a voltage sweep of a voltage variable capacitor to adjust the RF sensor to match the RF signal being emitted by the MRI. This improves RF detection by automatically adjusting the RF sensor to the RF frequency of the MRI machine.

In a different embodiment the tunable RF sensor 115, 116 would require prior programming to match the RF output of the MRI or other RF emitting instrument. This would require an external device 102 to tune the RF sensor 211 by selectively activating the required capacitors.

For as long as the controller 230 continues to detect the presence of both the magnetic field and RF signals (i.e., the logical AND operation), the controller 230 activates or opens the switches 821C–821F of the switch bank 820. In particular, the controller 230 may be configured to open switches 821C–821F during the duration of each detected RF pulse so that the controller 230 may continue to control the patient-supporting operations such as pacing, cardioverting, and defibrillation.

When the controller 230 activates and opens the switches 821C–821F due to the presence of undesirable magnetic field and RF signal, the implanted electrodes 22–23, 25–28, 32, 34, 36, and 38 may be shielded from the pulse generators 70, 72, so as to eliminate the formation of induction loops. During this isolation period, however, the controller 230 could lose its capability to send and receive signals to and from other components of the implantable device. To this end, another exemplary dynamic isolation system may incorporate the ability to switch out of the isolation mode for preset intervals despite the presence of undesirable external magnetic field or RF signal so that the implanted device 10 could resume its normal functions, such as normal sensing operations, pacing, cardioverting or defibrillation.

Figure 9:
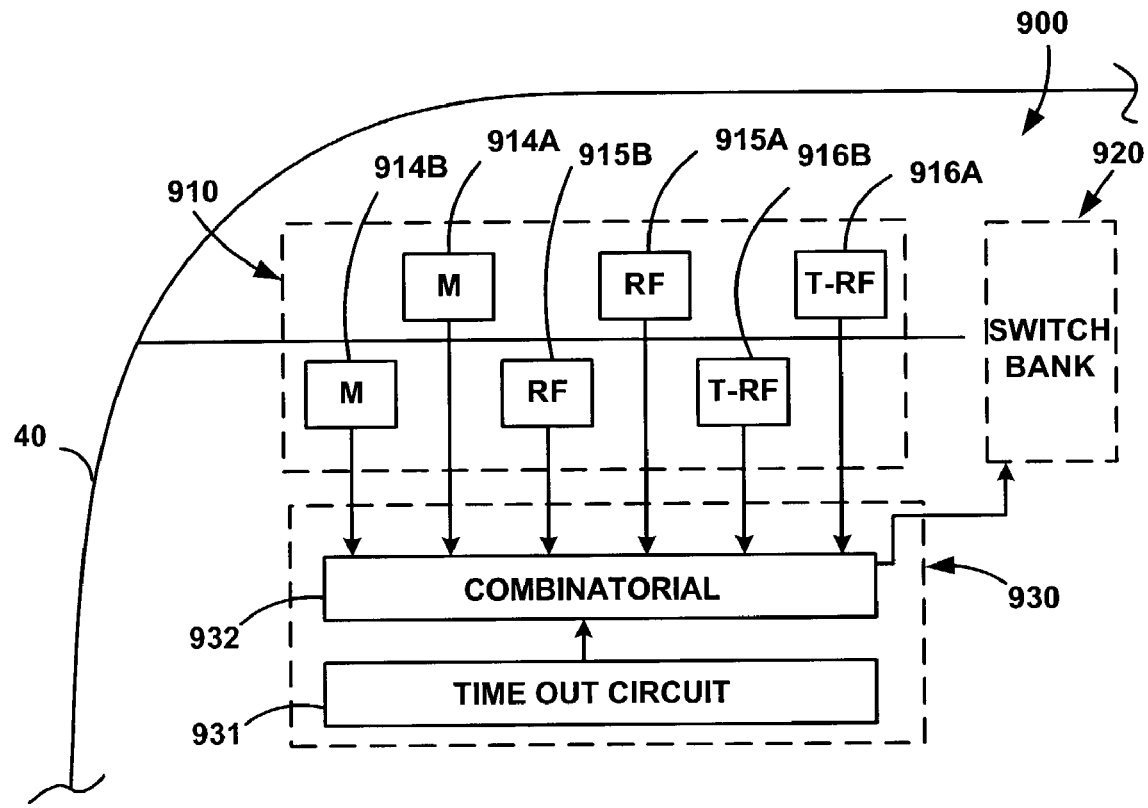
FIG. 9 represents an exemplary high level system diagram of a dynamic isolation system of the present invention.

FIG. 9 represents an exemplary high level system diagram of the dynamic isolation system 700 or 800 of the stimulation device 10, which is represented by the reference numeral 900. The isolation system 900 comprises a time-out circuit 931 and a combinatorial logic 932 that form part of the controller 930, a sensor unit 910, and a switch bank 920. The switch bank 920 is generally similar in function to the switch bank 720 of FIG. 7 and the switch bank 820 of FIG. 8, and is referenced by the numeral 920.

The combinatorial logic 932 is coupled to the switch bank 920 to control the actuation (i.e., opening and closing) of switches 721A–721B (FIG. 7) or switches 821C–821F (FIG. 8) of the switch bank 920. The time-out unit 931 is configured to count elapsed time after the switches 721A–721B or 821C–821F are opened (i.e., activated) or closed (i.e., deactivated) by the combinatorial logic 932.

The sensor unit 910 is comprised of a plurality of sensors, such as magnetic field sensors 914A, 914B, RF sensors 915A, 915B, and tuned RF sensors 916A, 916B. While specific sensors are illustrated in FIG. 9, it should be understood that any number of magnetic field sensors and/or tuned and non-tuned RF sensors can be used, and appropriately disposed relative to the housing 40. However, as described earlier, the dynamic isolation system 900 may desirably include at least one magnetic field sensor and at least one RF sensor to minimize false detection of external magnetic fields and RF signals.

In operation, the sensors 914A, 914B, 915A, 915B, 916A, and 916B detect the presence of external magnetic fields or RF signals. If the intensities of these magnetic fields or RF signals exceed corresponding preset limits, the controller 930 activates both of switches 721A, 721B for the embodiment of FIG. 7 or all the switches 821C–821F for the embodiment of FIG. 8, to eliminate high-frequency and low-frequency induction currents.

The controller 930 preferably activates the I/O switches 821CD–821F (FIG. 8) according to a combinatorial logic wherein both the magnetic field sensors 914A, 914B and at least one of the RF sensors 915A, 915B, 916A, 916B register the presence of an undesirable magnetic field and undesirable RF signals, respectively. The time-out circuit 931 keeps track of the elapsed time upon actuation of the I/O switches 821C–821F or 721A–721B. When the I/O switches 821C–821F remain open beyond a preset isolation duration, the time-out circuit 931 switches the dynamic isolation system 900 out of the isolation mode by closing the I/O switches 821C–821F to allow the controller 930 to perform its normal functions. Accordingly, the time-out circuit 931 may limit the duration of the I/O switches 821C–821F in the isolation mode to prevent excessive or inappropriate duration of pacing and sensing inhibition.

When the implantable device has performed its normal sensing, pacing, cardioverting, and/or defibrillating operation, the dynamic isolation switching would be re-activated provided the required sensors 915A, 915B, 916A, 916B register the presence of an undesirable magnetic field and undesirable RF signals, respectively. The cycle would then be repeated as necessary to protect the patient from induced currents while allowing normal device function. Alternatively, the time-out circuit 931 may instruct the controller 930 to determine the proper ensuing action. The time-out circuit 931 is generally configured to be re-initialized each time the I/O switches 821C–821F are actuated. This feature ensures pacing- and sensing-dependent patients to receive proper life-sustaining therapies.

Figure 10:
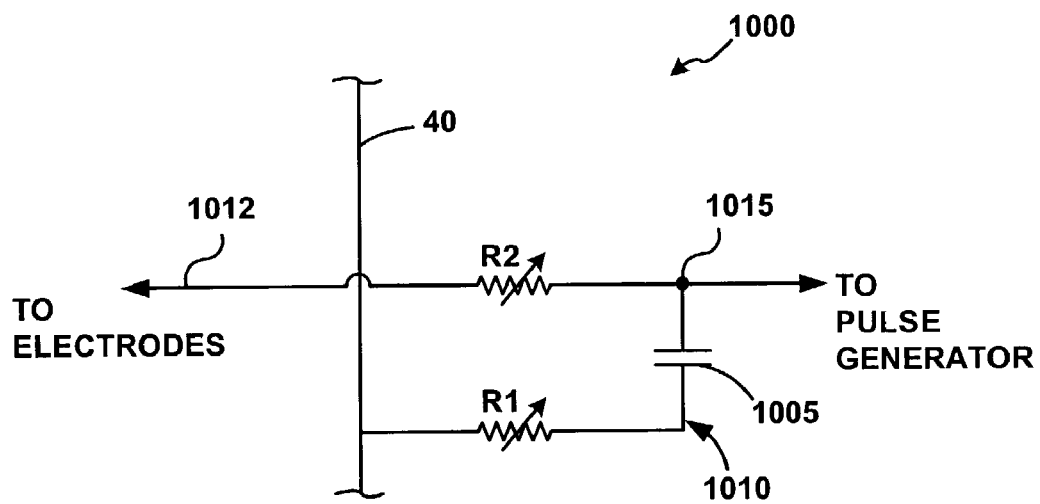
FIG. 10 is a circuit diagram of an exemplary dynamic isolation system with multiple magnetoresistors according to the present invention.

FIG. 10 illustrates another aspect of the present invention, according to which a dynamic isolation system 1000 can prevent, or at least minimize induction currents generated by high-frequency RF signals. The isolation system 1000 couples magnetoresistors R1 and R2 to a feedthrough 1005. Advantageously, this embodiment may readily be applied to existing stimulation devices without the need to include, for example, the non-filtered feedthroughs 712A–712B of FIG. 7, 812C–812D of FIG. 8, switches 721A–721B of the switch bank 720 (FIG. 7), switches 821C–821F of the switch bank 820 (FIG. 8), and sensors 914A, 914B, 915A, 915B, 916A, and 916B of the sensor unit 910 (FIG. 9).

In the dynamic isolation system 1000, a connection wire 1010 couples the housing 40 of the stimulation device 10 to an electrode lead 1012 at junction 1015. A first magnetoresistor (R1) and the filtered feedthrough 1005 are connected in series between junction 1015 and the housing 40, and are disposed inside the housing 40. An optional second magnetoresistor (R2) can be connected between junction 1015 and the electrode lead 1012, and is also disposed inside the housing 40.

In operation, the conventional filtered feedthrough 1005 filters the interference resulting from weak or normal magnetic fields or RF signals in a normal mode. When the dynamic isolation system 1000 is subjected to strong magnetic fields exceeding for example approximately 2 teslas, the resistances of the magnetoresistors R1 and R2 are increased up to about 40 times. Accordingly, the induction currents flowing through the lead 1012 and the filtered feedthrough 1005 can be reduced dramatically. The preferable resistances of the magnetoresistors R1 and R2 are generally approximately 50Ω and 100Ω for a pacing operation, respectively (which will be increased to 2 KΩ and 4Ω, respectively, in the 2-telsa magnetic field).

According to still another embodiment, the isolation system of the present invention includes an RF sensor that is capable of detecting EMI in three dimensions through the use of coils orientated in each dimensional plane. Thus, various systems and methods therefor using static isolation systems and dynamic isolation systems in implantable cardiac stimulation devices have been described in which the pulse generators and electrode leads are insulated or isolated to eliminate or interrupt the flow of induction currents. While detailed descriptions of the specific embodiments of this invention have been provided, it would be apparent to those skilled in the art that numerous variations of the systems and methods described herein may be possible in which the concepts of this invention may readily be applied. The descriptions provided herein are for the sake of illustration and in no aspect intended to be exclusive.

What is claimed is:

1. An implantable cardiac device comprising:
   internal circuitry;
   a housing that encases the internal circuitry;
   a conductor connected to the internal circuitry;
   an isolation system comprising:
   a sensor unit that detects a presence of a magnetic field;
   at least one non-filtered feedthrough that prevents a current induction loop from forming between the conductor and the housing;
   at least one filtered feedthrough disposed within the housing and that protects the internal circuitry; and
   a switch bank disposed inside the housing, between the non-filtered feedthrough and the filtered feedthrough, and connected to the sensor unit, to selectively disconnect an electrical conduction path from the conductor to the internal circuitry, upon sensing the presence of a predetermined magnetic field by the sensor unit;
   a controller disposed within the housing, that is coupled to the sensor unit, and that operatively controls the switch bank;
   wherein the sensor unit comprises a magnetic field sensor;
   wherein the sensor unit further comprises a tunable radio frequency sensor that further detects the presence of a radio frequency signal;
   wherein the sensor unit detects the presence of any of the magnetic field or the radio frequency signal continuously; and
   wherein if the magnetic field sensor detects a presence of a high-Tesla magnetic field, the controller initiates a voltage sweep to adjust the tunable radio frequency sensor to match the radio frequency of the detected high-Tesla magnetic field.

2. The implantable cardiac device of claim 1, wherein the switch bank selectively disconnects the conduction path upon sensing the presence of the radio frequency signal by the radio frequency sensor.

3. The implantable cardiac device of claim 1, wherein the sensor unit further comprises a first radio sensor and a second radio frequency sensor;
   wherein the magnetic field sensor and the first radio frequency sensor are disposed within the sealed compartment; and
   wherein the second frequency sensor is disposed within the header.

4. The implantable cardiac device of claim 1, wherein the sensor unit detects the presence of any of the magnetic field or the radio frequency signal upon the controller receiving a command signal.

5. The implantable cardiac device of claim 1, wherein the switch bank comprises a switch; and
wherein the controller causes the switch to open upon sensing the presence of the magnetic field.

6. The implantable cardiac device of claim 1, wherein the switch bank comprises a switch; and
wherein the controller causes the switch to open upon sensing the presence of the radio frequency signal.

7. The implantable cardiac device of claim 1, wherein the magnetic field is an external magnetic field generated by magnetic resonance imaging.

8. The implantable cardiac device of claim 1, wherein the radio frequency signal is an external radio frequency signal generated by electromagnetic interference.

9. The implantable cardiac device of claim 1, wherein the internal circuitry comprises a pulse generator; and
further comprising an insulation coating that encapsulates the housing, at least in part, to attenuate the intensify of a sensed induction current to the pulse generator.

10. The implantable cardiac device of claim 1, further comprising a timing circuitry that prevents excessive duration of induction loop interruption.

11. The implantable cardiac device of claim 1, wherein the isolation system further comprises an attenuation system disposed in series with a non-filtered feedthrough.

12. The implantable cardiac device of claim 11, wherein the attenuation system comprises at least one magnetoresistor.

13. The implantable cardiac device of claim 1, wherein the tunable radio frequency sensor is a swept radio frequency detector to tune radio frequency signals with multiple preselected frequencies to sense radio frequency signals at those frequencies.

14. An implantable cardiac device comprising:
internal circuitry;
a housing that encases the internal circuitry;
a conductor connected to the internal circuitry;
an isolation system comprising:
a sensor unit that detects a presence of a magnetic field;
at least one non-filtered feedthrough that prevents a current induction loop from forming between the conductor and the housing;
at least one filtered feedthrough disposed within the housing and that protects the internal circuitry; and
a switch bank disposed inside the housing, between the non-filtered feedthrough and the filtered feedthrough, and connected to the sensor unit, to selectively disconnect an electrical conduction path from the conductor to the internal circuitry, upon sensing the presence of a predetermined magnetic field by the sensor unit;
a controller disposed within the housing, that is coupled to the sensor unit, and that operatively controls the switch bank;
wherein the sensor unit comprises a magnetic field sensor;
wherein the sensor unit further comprises a tunable radio frequency sensor that further detects the presence of a radio frequency signal;
wherein the sensor unit detects the presence of any of the magnetic field or the radio frequency signal periodically; and
wherein if the magnetic field sensor detects a presence of a high-Tesla magnetic field, the controller initiates a voltage sweep to adjust the tunable radio frequency sensor to match the radio frequency of the detected high-Tesla magnetic field.

15. The implantable cardiac device of claim 14, wherein the tunable radio frequency sensor is a swept radio frequency detector to tune radio frequency signals with multiple preselected frequencies to sense radio frequency signals at those frequencies.

16. An implantable cardiac device comprising:
internal circuitry;
a housing that encases the internal circuitry;
a conductor connected to the internal circuitry;
an isolation system comprising:
a sensor unit that detects a presence of a magnetic field;
at least one non-filtered feedthrough that prevents a current induction loop from forming between the conductor and the housing;
at least one filtered feedthrough disposed within the housing and that protects the internal circuitry; and
a switch bank disposed inside the housing, between the non-filtered feedthrough and the filtered feedthrough, and connected to the sensor unit, to selectively disconnect an electrical conduction path from the conductor to the internal circuitry, upon sensing the presence of a predetermined magnetic field by the sensor unit;
a controller disposed within the housing, that is coupled to the sensor unit, and that operatively controls the switch bank;
wherein the sensor unit comprises a magnetic field sensor;
wherein the sensor unit further comprises a radio frequency sensor that further detects the presence of a radio frequency signal;
wherein the sensor unit comprises a tunable radio frequency sensor; and
wherein if the magnetic field sensor detects a presence of a high-Tesla magnetic field, the controller initiates a voltage sweep to adjust the radio frequency sensor to match the radio frequency of the detected high-Tesla magnetic field.

17. The implantable cardiac device of claim 15, wherein the tunable radio frequency sensor is a swept radio frequency detector to tune radio frequency signals with multiple preselected frequencies to sense radio frequency signals at those frequencies.

18. An implantable cardiac device comprising:
internal circuitry;
a housing that encases the internal circuitry;
a conductor connected to the internal circuitry;
an isolation system comprising:
a sensor unit that detects a presence of a magnetic field;
at least one non-filtered feedthrough that prevents a current induction loop from forming between the conductor and the housing;
at least one filtered feedthrough disposed within the housing and that protects the internal circuitry; and
a switch bank disposed inside the housing, between the non-filtered feedthrough and the filtered feedthrough, and connected to the sensor unit, to selectively disconnect an electrical conduction path from the conductor to the internal circuitry, upon sensing the presence of a predetermined magnetic field by the sensor unit;
a controller disposed within the housing, that is coupled to the sensor unit, and that operatively controls the switch bank;
wherein the sensor unit comprises a magnetic field sensor;
wherein the sensor unit further comprises a tunable radio frequency sensor that further detects the presence of a radio frequency signal;

wherein the tunable radio frequency sensor is capable of detecting electromagnetic interference in three dimensions; and wherein if the magnetic field sensor detects a presence of a high-Tesla magnetic field, the controller initiates a voltage sweep to adjust the tunable radio frequency sensor to match the radio frequency of the detected high-Tesla magnetic field.

19. The implantable cardiac device of claim 18, wherein the tunable radio frequency sensor is a swept radio frequency detector to tune radio frequency signals with multiple preselected frequencies to sense radio frequency signals at those frequencies.

* * * * *